(12) United States Patent
Besio (10) Patent No.: US 8,626,259 B2
(45) Date of Patent: Jan. 7, 2014

(54) BIOMEDICAL SENSORS USABLE ON UN-PREPARED CONTACT SURFACES (75) Inventor: Walter G Besio, Kingston, RI (US)

(73) Assignee: Board of Governors For Higher Education, State of Rhode Island And Providence Plantations, Providence, RI (US)

(*) Notice: Subject to any disclaimer, the term of this patent is extended or adjusted under 35 U.S.C. 154(b) by 0 days.

(21) Appl. No.: 12/908,065

(22) Filed: Oct. 20, 2010

(65) Prior Publication Data
US 2011/0054288 A1 Mar. 3, 2011

Related U.S. Application Data (63) Continuation of application No. PCT/US2009/041924, filed on Apr. 28, 2009.

(60) Provisional application No. 61/048,672, filed on Apr. 29, 2008.

(51) Int. Cl.
A61B 5/0476 (2006.01)
A61B 5/0478 (2006.01)

(52) U.S. Cl.
USPC .............. 600/383; 600/393; 600/544

(58) Field of Classification Search
CPC .................................... A61B 5/0478
USPC .......................... 600/383, 544, 393
See application file for complete search history.

(56) References Cited

U.S. PATENT DOCUMENTS

| 4,084,583 | A | | 4/1978 | Hjort |
| 4,275,743 | A | | 6/1981 | Hjort |
| 4,457,309 | A | * | 7/1984 | Elmeskog ............ 600/382 |
| 4,550,735 | A | | 11/1985 | Akamatsu et al. |
| 4,632,122 | A | * | 12/1986 | Johansson et al. ....... 600/383 |
| 4,709,702 | A | * | 12/1987 | Sherwin ............ 600/383 |
| 4,751,928 | A | * | 6/1988 | Hallon et al. ............ 600/382 |
| 5,305,746 | A | | 4/1994 | Fendrock |
| 6,032,064 | A | | 2/2000 | Devlin et al. |
| 6,073,039 | A | * | 6/2000 | Berson ............... 600/544 |

(Continued)

FOREIGN PATENT DOCUMENTS

DE 3025955 A1 1/1982
EP 1767147 A 1/2006

(Continued)

OTHER PUBLICATIONS

International Preliminary Report on Patentability based on International application No. PCT/US2009/041924 and with a filing date on Apr. 28, 2009, 8 pages.

(Continued)

Primary Examiner — Lee S Cohen
(74) Attorney, Agent, or Firm — Gesmer Updegrove LLP (57) ABSTRACT A biomedical sensor is disclosed that provides at least first and second electrical nodes for connection to medical equipment. The biomedical sensor includes a plurality of protruding electrodes that extend from a common base. At least one of the protruding electrodes is coupled to the first electrical node, and at least two of the protruding electrodes are coupled to the second electrical node. At least one of the plurality of protruding electrodes is adjustable in length such that each of the plurality of protruding electrodes is adapted to contact a non-planar surface of a subject.

29 Claims, 7 Drawing Sheets

(56) References Cited

U.S. PATENT DOCUMENTS

| | | | |
|---|---|---|---|
| 6,280,454 B1* | 8/2001 | Wang | 600/383 |
| 6,574,513 B1 | 6/2003 | Collura et al. | |
| 7,054,681 B2* | 5/2006 | Husar et al. | 600/544 |
| 7,286,871 B2 | 10/2007 | Cohen | |
| 7,738,939 B2* | 6/2010 | Hallin | 600/393 |
| 2003/0187490 A1 | 10/2003 | Gliner | |
| 2004/0199237 A1 | 10/2004 | Mills et al. | |
| 2006/0173510 A1* | 8/2006 | Besio et al. | 607/45 |
| 2007/0238945 A1* | 10/2007 | Delic et al. | 600/383 |
| 2007/0255127 A1* | 11/2007 | Mintz et al. | 600/383 |
| 2008/0154112 A1 | 6/2008 | Murphy et al. | |
| 2009/0005667 A1 | 1/2009 | Cui et al. | |
| 2009/0030298 A1 | 1/2009 | Matthews et al. | |
| 2010/0198042 A1* | 8/2010 | Popescu et al. | 600/383 |

FOREIGN PATENT DOCUMENTS

| | | |
|---|---|---|
| WO | WO2008009761 A | 1/2008 |
| WO | WO2008/067839 A | 6/2008 |
| WO | WO2006060727 | 6/2008 |

OTHER PUBLICATIONS

Koka et al., Improvement of Spatial Selectivity and Decrease of Mutual Information of Tri-Polar Concentric Ring Electrodes, Journal of Neuroscience Methods, 2007, pp. 216-222, vol. 165, Elsevier Science, USA.

Besio et al., Development of a Tri-Polar Concentric Ring Electrode for Acquiring Accurate Laplacian Body Surface Potentials, Annals of Biomedical Engineering, Mar. 2006, pp. 426-435, vol. 34, No. 3, Biomedical Engineering Society, USA.

Besio et al., Tri-Polar Concentric Ring Electrode Development for Laplacian Electroencephalography, IEEE Transactions on Biomedical Engineering, May 2006, pp. 926-933, vol. 53, No. 5, IEEE, USA.

Besio et al., Mutual Information of Tri-Polar Concentric Ring Electrodes, Proceedings of the 28th IEEE EMBS Annual International Conference, 2006, pp. 1-4, NYC, USA.

Besio et al., Simulated Comparison of Disc and Concentric Electrode maps During Atrial Arrhythmias, Journal of Bioelectromagnetism, 2005,pp. 217-220, vol. 7 No. 1, USA.

Besio et al., Application of Tripolar Concentric Electrodes and Pre-Feature Selection Algorithm for Brain-Computer Interface, IEEE Trans Neural Systems Rehabilitation Engineering, 2007, pp. 1-8, USA.

Besio et al., Tripolar Laplacian electrocardiogram and moment of activation isochronal mapping, Physiological Measurement, 2007, pp. 515-529, vol. 28, IOP Publishing, USA.

Liu et al., A Modeling Study Comparing the Signal-To-Noise Ratio Between Tripolar Concentric Ring and Conventional Disk Electrodes With Added Common-Mode Noise, University of Rhode Island, 2 pages, USA.

Warner, http://www.warneronline.com/contact_us.cfm, accessed Apr. 10, 2008, 1 page, USA.

Medcompare, http://www.medcompare.com/details/34697/Single-Disc-Electrodes.html, retrieved Dec. 20, 2010, 2 pages, USA.

Easy Cap, http://www.easycap.de/easycap/e/products/products.htm, retrieved Dec. 20, 2010, 9 pages, USA.

Mind Media, http://www.mindmedia.nl/english/electrodes.php, retrieved Dec. 20, 2010, 3 pages, USA.

BNET, http://findarticles.com/p/articles/mi_m0EIN/is_2005_August_30/ai_n14937127, Astro-Med Product Selected for New Video-EEG Applications, retrieved Dec. 20, 2010, 2 pages, USA.

"Variable-Impedance Electrode System, with Fixed Relative Lead Layout and Motion Sensors, for Electrophysiological Recordings During MRI", Knowledge Express, Subscription Required, 1 page.

Article: Simulation Evaluates Combined EEG/MRI Safety, Electromagnetic News Report, http://highbeam.com/doc/1P3-1090052731.html, Jul. 1, 2006, 2 pages, USA.

International Search Report based on International Application No. PCT/US2009/041924 with an International Filing date of Apr. 28, 2009, 14 pages, USA.

Natus Medical Incorporated (Baby.O) Company Profile, www.reuters.com/finance/stocks/companyProfile? symbol=Baby.O, retrieved Dec. 23, 2010, 1 page, USA.

Grass Technologies, Genuine Grass Precious Metal Recording Electrodes, www.grasstechnologies.com/products/electrodes/electprecious1.html, retrieved Dec. 23, 2010, 2 pages, USA.

Farina et al., Concentric-Ring Electrode Systems for Noninvasive Detection of Single Motor Unit Activity, IEEE Transactions on Biomedical Engineering, 2001, pp. 1326-1334, vol. 48, No. 11, IEEE, Italy.

He et al., Body Surface Laplacian Mapping in Man, Annual International Conference of the IEEE Engineering in Medicine and Biology Society, 1991, pp. 0784-0786, vol. 13, No. 2, IEEE, USA.

He et al., Body Surface Laplacian ECG Mapping, IEEE Transactions on Biomedical Engineering, 1992, pp. 1179-1191, vol. 39, No. 11, IEEE, USA.

Huiskamp, Difference Formulas for the Surface Laplacian on a Triangulated Surface, Journal of Computational Physics, 1991, pp. 477-493, Academic Press, The Netherlands.

Oosterom et al., Computing the lead field of electrodes with axial symmetry, Medical & Biological Engineering & Computing, 1983, pp. 473-481, vol. 21, IFMBE, The Netherlands.

\* cited by examiner

BIOMEDICAL SENSORS USABLE ON UN-PREPARED CONTACT SURFACES

PRIORITY

The present application is a continuation application of PCT/US2009/041924 filed on Apr. 28, 2009, which claims priority to U.S. Provisional Patent Application Ser. No. 61/048,672 filed Apr. 29, 2008, the entire disclosure of which is hereby incorporated by reference.

BACKGROUND

The invention generally relates to biomedical sensors and relates in particular to biomedical sensors for detecting localized electrical signals within a subject.

Conventional disc biomedical sensors have generally changed little since Hans Berger first recorded the human electroencephalogram (EEG) in 1924. One drawback of conventional EEG methods that are recorded with disc electrodes, is that the procedure lacks high spatial resolution. This is primarily due to the blurring affects of the different conductivities of the volume conductor such as the cerebrospinal fluid, skull, and the scalp. Conventional EEG signals recorded with disc electrodes also have reference electrode problems as idealized references are not available with EEG. Placing the reference at different locations changes the characteristics of the EEG signals.

To increase the spatial frequency and selectivity the surface Laplacian has been utilized. Concentric ring electrodes automatically estimate the surface Laplacian significantly better than by processing conventional EEG signals (See "Development of Tri-Polar Concentric Ring Electrode for Acquiring Accurate Laplacian Body Surface Potentials", by W. Besio, R. Aakula, K. Koka and W. Dai, *Annals of Biomedical Engineering*, Vol. 34, No. 3, March 2006) and significantly improves the signal-to-noise level in EEG applications, (see "Tri-Polar Concentric Ring Electrode Development for Laplacian Electroencephalography, by W. Besio, R. Aakula, K. Koka and W. Dai, *IEEE Transactions on Biomedical Engineering*, Vol. 53, No. 5, May 2006), as well as spatial selectivity, and mutual information (see "*Improvement of Spatial Selectivity and Decrease of Mutual Information of Tri-Polar Concentric Ring Electrodes*", by K. Koka and W. Besio, *Journal of Neuroscience Methods*, Vol. 165, pp. 216-222, Jun. 9, 2007). The reference problem is alleviated as well since bipolar differences are taken at closely spaced electrode elements. The presence of hair however, remains a concern limiting the surface where the electrodes can make contact with the scalp without shaving.

Typically, an electrode gel (e.g., an electrolyte) has been used to bridge between electrodes and a cleaned surface of a subject (e.g., the scalp). The thickness of the gel varies with different applications, causing varying electrical properties with different applications. The gel also dries over time further changing the properties of the bridge distorting the EEG. Such gels must also be packaged in sealed packages to avoid becoming dried out prior to being used and may not be reused once opened. Gels may also irritate the scalp and/or the desired recording may be from a sensitive area of the subject, such as the eye, where the use of gel should be avoided. Further, if the spacing of electrodes is too small then the gel, which is typically an electrolyte, may directly connect the electrodes, shorting the sensor. Also, the application and removal of gels is time consuming.

Further, the spacing required between electrodes may be so small that smearing of the electrolyte (and thus short circuiting of the bioelectric signal) may occur. Additionally, and perhaps most importantly, the application and removal of electrolyte gels is an unpleasant process for the subject, and time consuming for the clinician or care giver. There are also toxicological concerns with electrolyte gels where dermatological responses are common.

To avoid the problems of electrolytes, dry electrodes (not using a gel) have been introduced. With dry electrodes, however, movement artifacts are more prevalent due to the absence of a thick electrolyte layer (as is present in gels, which provides a shock absorber function). The introduction of active electrodes (where buffering/amplification takes place at the electrode site) provides much less emphasis on the skin-electrode impedance. An added concern with dry electrodes is that the large RC constant, which exists at the input of the unity gain amplifiers typically used for this application, prolongs the effect of large artifacts.

There is a need therefore, for an improved biomedical sensor that may be used without the current drawbacks of using a gel yet may also provide consistent and reliable signals.

SUMMARY

The invention provides a biomedical sensor that provides at least first and second electrical nodes for connection to medical equipment. The biomedical sensor includes a plurality of protruding electrodes that extend from a common base. In accordance an embodiment, at least one of the protruding electrodes is coupled to the first electrical node, and at least two of the protruding electrodes are coupled to the second electrical node. At least one of the plurality of protruding electrodes is adjustable in length such that each of the plurality of protruding electrodes is adapted to contact a non-planar surface of a subject.

In accordance with a further embodiment, the plurality of protruding electrodes are spaced from one another such that the protruding electrodes are adapted to contact a surface of a subject without interference by material that is attached to the contacting surface of the subject.

In accordance with a further embodiment, at least one of the protruding electrodes is coupled to the first electrical node, at least one of the protruding electrode is coupled to the second electrical node, and at least one protruding electrode is coupled to a third electrical node. The plurality of protruding electrodes are spaced from one another such that the protruding electrodes are adapted to contact a surface of a subject without interference by material that is attached to the contacting surface of the subject.

In accordance with a further embodiment, the invention provides a method of applying a biomedical sensor to a patient. The biomedical sensor provides at least first and second electrical nodes for connection to medical equipment, and the biomedical sensor includes a plurality of protruding electrodes that extend from a common base. The method includes the steps of coupling at least some of the plurality of protruding electrodes to the first electrical node, coupling at least some of the plurality of protruding electrodes to the second electrical node, contacting a site of a subject with distal ends of each of the plurality of protruding electrodes, and coupling the first and second electrical nodes to the medical equipment. The step of contacting the site of the subject includes passing distal ends of each of the plurality of protruding electrodes through material that is attached to a contacting surface at the site of the subject. In accordance with a further embodiment, the step of contacting the site of the subject includes adjusting the length of at least one of the plurality of protruding electrodes such that each of the plurality of protruding electrodes contacts a non-planar surface at the site of the subject.

BRIEF DESCRIPTION OF THE ILLUSTRATED EMBODIMENTS

The following description may be further understood with reference to the accompanying drawings in which.

The drawings are shown for illustrative purposes only.

DETAILED DESCRIPTION

Figure 1:
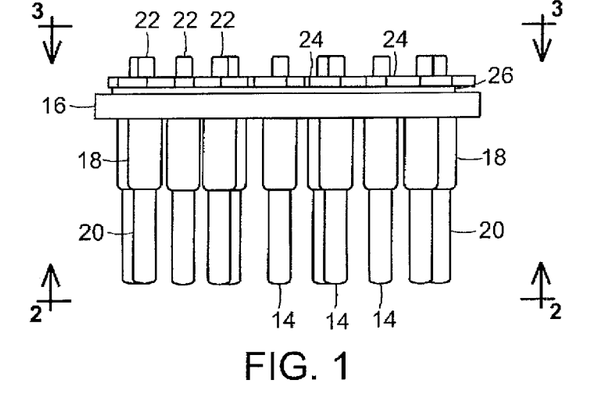
FIG. 1 shows an illustrative diagrammatic view of a biomedical sensor in accordance with an embodiment of the invention.
Figure 2:
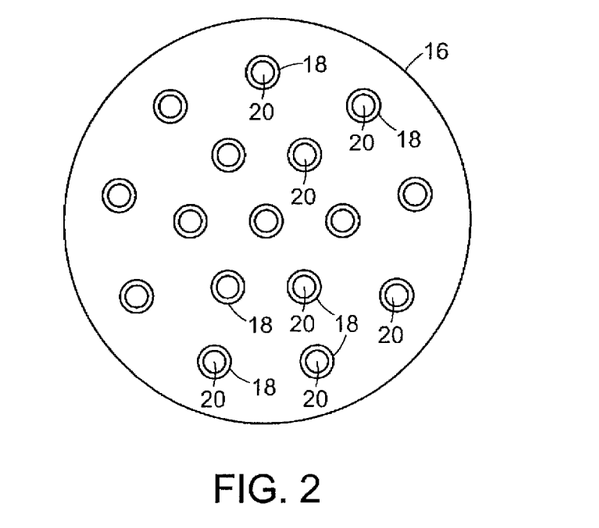
FIG. 2 shows an illustrative diagrammatic bottom view of the biomedical sensor of FIG. 1 taken along line 2-2 thereof.

As shown in FIG. 1, the invention provides a biomedical sensor 10 in accordance with an embodiment that includes a plurality of protruding electrodes 14 that extend through and protrude from a common base 16. Each electrode includes a fixed protruding portion 18 and a resilient protruding portion 20 that extends from the fixed protruding portion 18 as further shown in FIG. 2, which shows a bottom view. As further shown in FIG. 3 (which shows a top view), each electrode also includes a mounting post 22 that extends through the base 16. Each mounting post 22 is threaded, and a nut 24 is used to fasten each electrode onto the base 16 as further shown in FIG. 4. In accordance with further embodiments, each protruding electrode may be attached to the base by a variety of known techniques, including for example, using solder, glue and/or press fit insertion.

Figure 3:
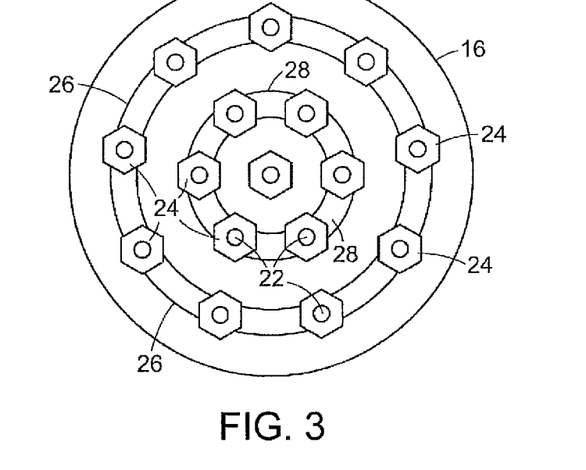
FIG. 3 shows an illustrative diagrammatic top view of the biomedical sensor of FIG. 1 taken along line 3-3 thereof.
Figure 4:
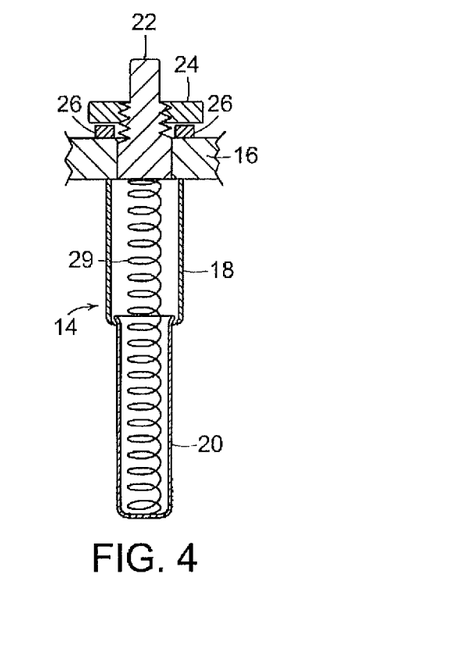
FIG. 4 shows an illustrative diagrammatic cross-sectional view of one protruding electrode in the biomedical sensor of FIG. 1.

In accordance with various embodiments the protruding electrodes 14 may be connected to monitoring equipment in such a way that they remain electrically independent of one another, or in some embodiments, one or more groups of electrodes may be commonly coupled via conductors. For example, FIG. 3 shows a first outer conductor 26 that electrically joins together the outer ring of electrodes, as well as a second conductor 28 that electrically joins together an inner ring of electrodes. The innermost electrode is electrically independent of the others. Each conductor (e.g., 26) is coupled to its associated electrode 14 by being captured between the conductive fastening nut and the base 16 as shown in FIG. 4. Each electrode, therefore, is electrically conductive from the post 22, through the fixed and resilient protrusion sections 18 and 20. In accordance with further embodiments an electrically conductive material may also be included within each electrode to further enhance the electrical conductivity of each electrode.

Figure 5:
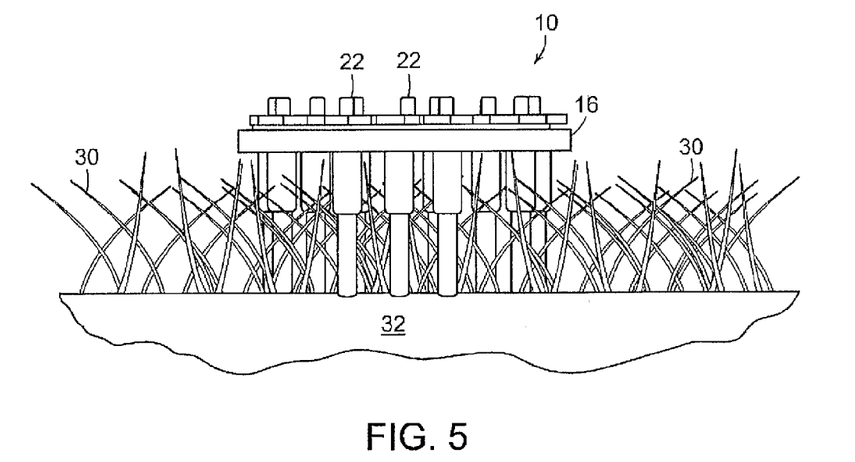
FIG. 5 shows an illustrative diagrammatic view of the biomedical sensor of FIG. 1 applied to a subject through hair.

The fixed and resilient protruding portions may pass through the hair on a subject, and the biomedical sensors of the invention may be used either with or without a gel. The individual electrodes, in accordance with an embodiment, are shaped of tubular rods such that the resilient protruding portion 20 penetrates through hair 30 reaching the scalp 32 of a subject as shown in FIG. 5. With reference as well to FIG. 4, there is force exerted on the resilient protruding portion, from inside the fixed protruding portion, keeping the electrode 14 in contact with the scalp 32. This force may be provided by a spring 29 in accordance with an embodiment. In further embodiments, such a force may be provided by any of a variety of techniques such as the use of pneumatic pressure within the protruding electrodes 14. In certain embodiments, spring loaded electrical connector pins such as the long-stroke spring-loaded pin product (product number 0914), sold by Mill-Max Mfg. Corp. of Oyster Bay, N.Y. may be used.

Figure 6:
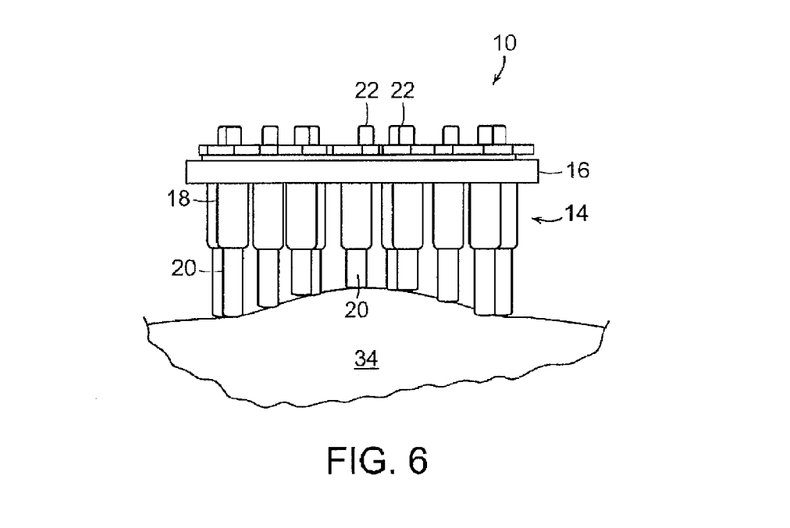
FIG. 6 shows an illustrative diagrammatic view of the biomedical sensor of FIG. 1 applied to a non-flat surface of a subject.

Another benefit of making the biomedical sensor out of independent protruding electrodes is that the force will keep the individual electrodes contacting the scalp even if the scalp is not flat. As shown in FIG. 6, the electrodes 14 will follow the contour of the scalp 34 or other body part to which the electrode is applied. Conversely, with a conventional solid ring, if there is a protrusion the ring may be raised up, not touching the scalp, altering the skin-to-electrode impedance. If a muscle contracts for example, protruding the skin upward below the surface of a conventional disc electrode, then part of the electrode may lose contact with the skin surface altering the skin-to-electrode impedance causing an artifact. Adding active electronics directly to the electrode matches the skin-to-electrode impedance better, permitting low impedance signals to be transmitted via wires to avoid AC power line interference. A conventional electrolytic gel may also be used to facilitate electrical conductivity with the subject.

During movements of the subject, therefore, the force on the electrodes will keep them in contact with the skin limiting signal loss or distortion from movement artifacts. As the shape of the skin changes, the independent elements automatically reshape to conform to the contour, retaining contact, reducing signal loss or distortion. In accordance with certain embodiments, a gel may be applied through the resilient protruding portion in accordance with an embodiment. Connecting the electrodes together in such a way as to provide effective concentric ring electrodes may be employed to achieve significantly better signal to noise ratios, spatial selectivity, approximation of the Laplacian, and mutual information, i.e., signals from areas of the subject that are outside of the target area of interest below the sensor. The virtual concentric electrodes would automatically attenuate distant sources such as eye blinks, jaw movements, ECG and ballistic ECG. Electrode preparation time will also be significantly improved.

Figure 7:
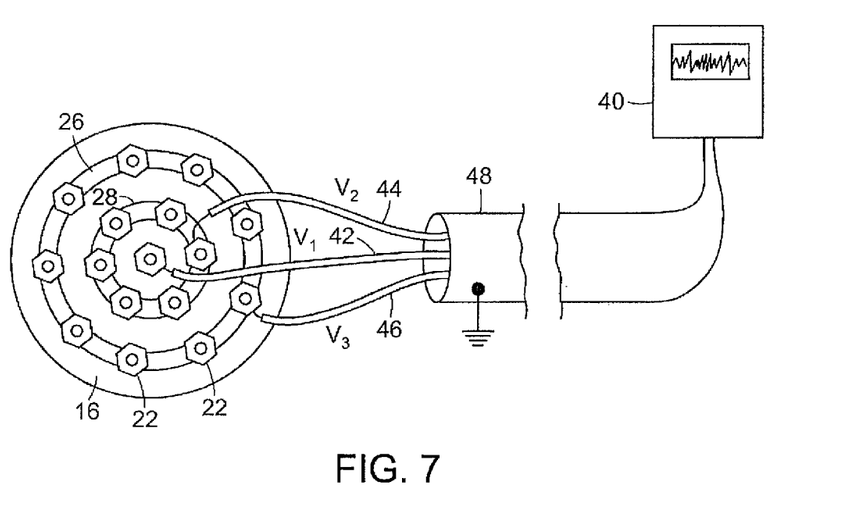
FIG. 7 shows an illustrative diagrammatic view of the biomedical sensor of FIG. 1 attached to monitoring equipment in accordance with an embodiment of the invention.

FIG. 7, for example, shows an embodiment of the invention in which an innermost electrode is coupled to monitoring equipment 40 via a first insulated wire 42. A group of electrodes is electrically coupled together by the second conductor 28, and are coupled to the monitoring equipment 40 by a second insulated wire 44. Another group of electrodes is electrically coupled together by the outer conductor 26, and are coupled to the monitoring equipment 40 by a third insulated wire 46. An outer sheath around the insulated wires 42, 44, 46 may also be grounded or may have some other signal applied to it for noise canceling.

Figure 8:
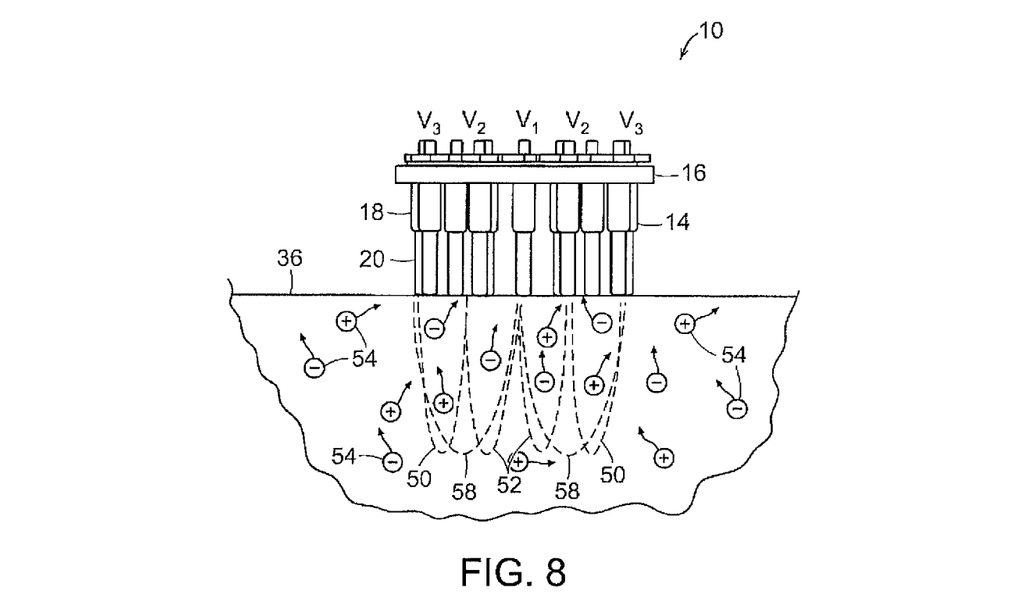
FIG. 8 shows an illustrative diagrammatic view of the biomedical sensor of FIG. 1 on an electrically active subject.

The use of the concentric electrodes at three different voltage nodes ($V_1$, $V_2$, $V_3$) provides that signals from the subject may be received and processed in a variety of ways. For example and with reference to FIG. 8, the outer ring of conductors may be employed to sense an outer region (as shown at 50) that surrounds the central region (as shown at 52), thereby providing a shielding function that prioritizes only signals directly below the sensor, while signals outside of the region shown at 50 will not contribute as much to the sensed signal since they are attenuated sharply. Other signals (such as shown at 54) will not contribute to the sensed signal. In further embodiments, the potentials between nodes $V_1$ and $V_3$ may be compared by sensing their difference (as shown at 58). In further embodiments, the differences between $V_1$ and $V_2$ as well as between $V_2$ and $V_3$ may also be determined.

For example, using a single conductivity planar model of the head the potentials on the electrode elements of a tripolar concentric ring electrode may be calculated as follows. The elements of the electrodes are divided into (for example 16 and 32) discrete points for the middle and outer rings, respectively with equal arclength between the points. The average was taken of all the discrete potentials as the potential for the element. A unity point source was moved from radius (r) r=0.0 cm to r=1.5 cm radially from the center of the electrode. The depth of the point source was 2.0 cm below the surface of the electrode. The calculated potentials from the disc, middle ring, and outer ring are $s_1(r)$, $s_2(r)$ and $s_3(r)$ respectively.

To improve the spatial sensitivity, and thereby the spatial resolution as much as possible, an algorithm may be derived to combine the three simulated signals to optimize the spatial cutoff. For this application the weights $w=[w_1, w_2, w_3]^T$ are adjusted, so that the magnitude of the signals in the region of interest, which is around $r=r_0$, where $r_0$ is an unknown radial distance to the source that we would like to detect and r is the radius from the tripolar concentric electrode, would be distinguished. To determine the weights minimum variance distortionless look (MVDL) beamformer may be employed to maximize P(w):

$$P(w) = \frac{\left(\sum_{i=1}^{3} x_i s_i(r_0)\right)^2}{\int_0^{r_{max}} \left(\sum_{i=1}^{3} w_i s_i(r)\right)^2 dr}$$

The sum x(r) is formed as follows:

$$x(r) = \sum_{i=1}^{3} w_i s_i(r)$$

where $w=[w_1, w_2, w_3]^T$ are the weights for the signals from the three different elements of the electrode. For the maximum output at $r=r0$ we constrain $x(r0)=1$ so that:

$$x(r_0) = \sum_{i=1}^{3} w_i s_i(r_0) = 1$$

Then, to maximize P(w), the value J(w) is minimized over $w=[w_1, w_2, w_3]^T$ where $$J(w) = \int_0^{r_{max}} \left(\sum_{i=1}^{3} w_i s_i(r)\right)^2 dr$$

To do this, let $s(r)=[s1(r), s2(r), s3(r)]T$ and $J(w)=w^T C w$ in which $$C = \int_0^{r_{max}} s(r) s^T C w$$

The value J(w) is then minimized, and the solution may be obtained from the above equations for $x(r_0)$ and for J(w) using the Lagrange multiplier approach:

$$F(w) = w^T C w + \lambda(w^T s(r_0) - 1)$$

where the following gradient is performed:

$$\frac{\partial F}{\partial w} = 2Cw + \lambda s(r_0) = 0$$

Since however, $x(r_0) = \sum_{i=1}^{3} w_i s_i(r_0) = 1$, which means $w^T s(r_0)=1$, then the solution takes the form of:

$$w_{opt} = \frac{C^{-1} s(r_0)}{s^T(r_0) C^{-1} s(r_0)}$$

and the combined signal is then:

$$x(r) = \frac{s^T(r) C^{-1} s(r_0)}{s^T(r_0) C^{-1} s(r_0)}$$

which is the optimized combination of the signals from the tripolar concentric ring electrode elements.

With the optimal combination showing the steepest roll-off and least ringing in the side lobes it should result in the best spatial resolution of the different methods. If the region of interest is directly under the electrode, and a source that is beyond the radius of the electrode by one radius (1.0 cm) then the Laplacian spatial filter will only pass approximately 10% of the power from that source, and the optimal combination attenuates nearly all of the power. A conventional disc electrode, on the other hand, is not vary discriminating as it would pass approximately 50% of the power of a source located in an area outside of the region of interest. For the tripolar concentric ring electrode Laplacian therefore, if the noise is correlated between the elements it is attenuated sharply. The MVDL beamformer appears to provide the optimal radial roll-off. This increased spatial sensitivity should also increase the spatial resolution of the tripolar concentric ring electrode.

Figure 9:
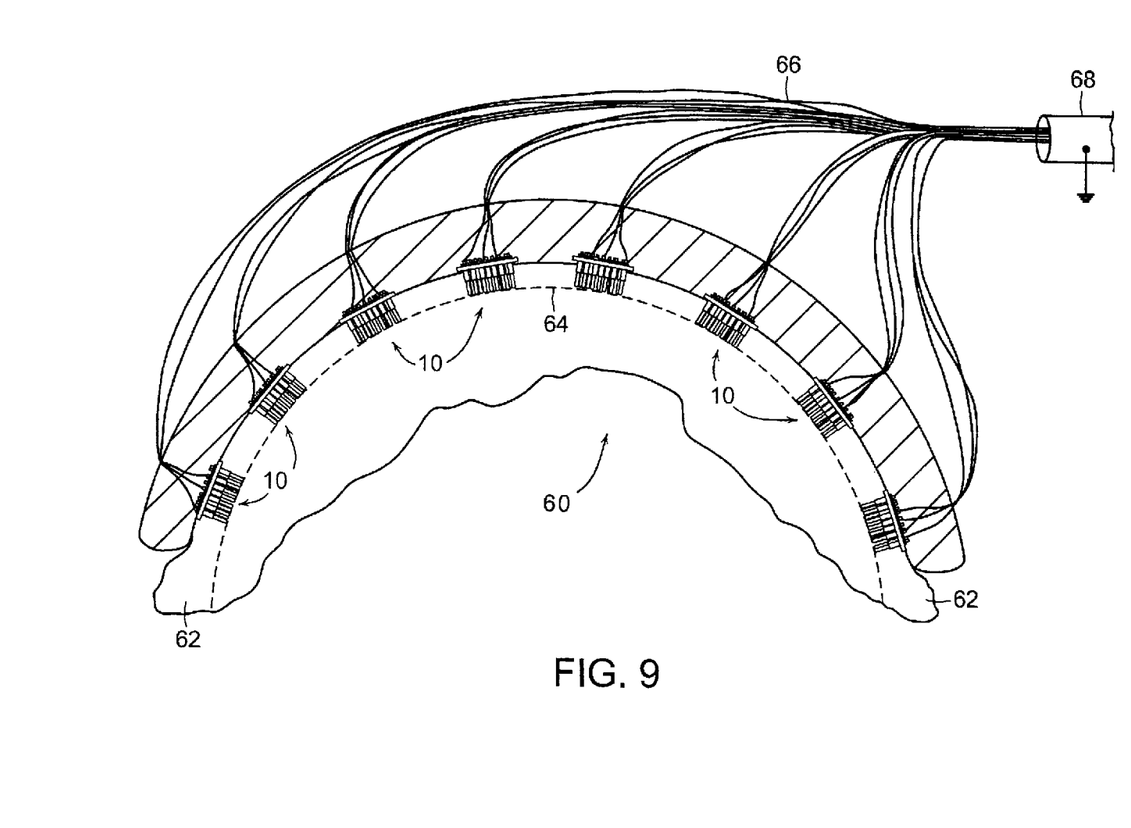
FIG. 9 shows an illustrative diagrammatic view of a biomedical monitoring device that includes many biomedical sensors.

The electrodes may be held in place on a subject by a variety of techniques, such as by using tape, a strap or a belt, or by securing the sensors to a structure that is held against the subject. For example, FIG. 9 shows a sectional view of a helmet 60 that includes a plurality of sensors 10 attached to the helmet 60. The sensors 10 each pass through hair 62 on the subject to contact the subject's scalp 64. Conductive wires from the sensors form a wiring harness 66 that is coupled to monitoring equipment. The Helmet 60 may be fitted to a subject's head, and the resilient protruding sections on the sensors permit the sensors to adjust to the contours of the patient's scalp. The helmet 60 may be held in place by a chin strap. In further embodiments, the helmet may include a wireless transceiver unit for providing signal data to the monitoring equipment without the need for a connector cable 68. This would permit a subject to be freely mobile during monitoring. The electrodes themselves may also each include wireless transmitters and/or receiver circuitry on each electrode.

Figure 10:
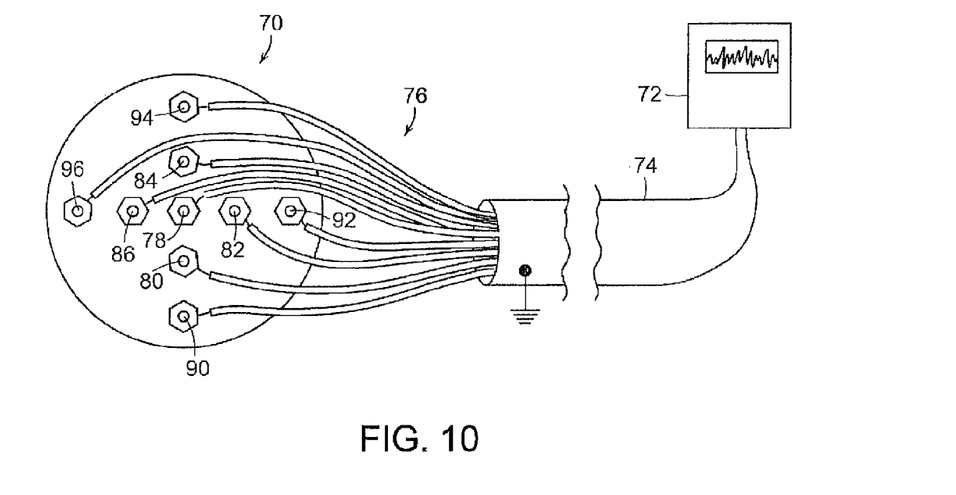
FIG. 10 shows an illustrative diagrammatic view of a biomedical sensor in accordance with another embodiment of the invention attached to monitoring equipment.

FIG. 10 shows a biomedical sensor 70 in accordance with another embodiment of the invention that is attached to biomedical monitoring equipment 72 via a cable 74 that includes multiple independent hard wire connections (as shown at 76) to each separate protruding electrode 78, 80, 82, 84, 86, 90, 92, 94, 96. Each protruding electrode is provided, therefore, as an independent electrical node. The signals from the electrodes may be analyzed in a variety of ways, including, for example, a five point method (using electrodes 78, 80, 82, 84 and 86), a nine point method (using electrodes 78, 80, 82, 84, 86, 90, 92, 94 and 96), and a quasi-bipolar method (wherein the electrodes 90, 92, 94 and 96 are electrically coupled together with electrode 78).

In particular and as further described in "Tri-Polar Concentric Ring Electrode Development for Laplacian Electroencephalography" by W. G. Besio, K. Koka, R. Aakula and W. Dai, *IEEE Transactions on Biomedical Engineering*, Vol. 53, No. 5, pp. 926-933 (May 2006), the disclosure of which is hereby incorporated by reference, several analytical techniques may be employed for determining an approximation to the Laplacian at the center of a tri-polar concentric ring electrode. For example, a five point method may be employed to analyze signals coming from one central point on a sensor as well as from each of four points that surround the central point. The Laplacian potentials at the central point ($P_0$) may be calculated to provide that the approximation to the Laplacian at $P_0$ is:

$$\Delta v_0 \cong \frac{4}{2r^2}(\bar{v} - v_0)$$

where $\bar{v} = (1/2\pi)\int_0^{2\pi} v(2\pi,\theta)d\theta$.

In another embodiment, a nine point method may be employed to analyze signals coming from one central point on a sensor, from each of four points that surround the central point, and from four more points that surround the first set of four points. The Laplacian potentials at the central point ($P_0$) may be calculated to provide that the approximation to the Laplacian at $P_0$ is:

$$\Delta v_0 \cong \frac{1}{3r^2}\left\{16\left(\frac{1}{2\pi}\int_0^{2\pi} v(r,\theta)d\theta - v_0\right) - \left(\frac{1}{2\pi}\int_0^{2\pi} v(2r,\theta)d\theta - v_0\right)\right\}$$

where $$\frac{1}{2\pi}\int_0^{2\pi} v(r,\theta)d\theta - v_0$$

represents the potential on the middle ring of a tri-polar configuration, and $$\frac{1}{2\pi}\int_0^{2\pi} v(2r,\theta)d\theta - v_0$$

represents the potential on the outer ring.

In a further embodiment, a quasi-bipolar method may be employed (wherein an outer ring and the center electrode are shorted together), and the Laplacian potential at $P_0$ is then calculated as:

$$\Delta v_0 \cong \frac{\bar{v} + v_0}{2} - v_m$$

where $\bar{v}$ is the average potential on the outer ring, $v_m$, is the average potential in the middle ring and $v_0$ is the average potential on the center electrode.

Figure 11:
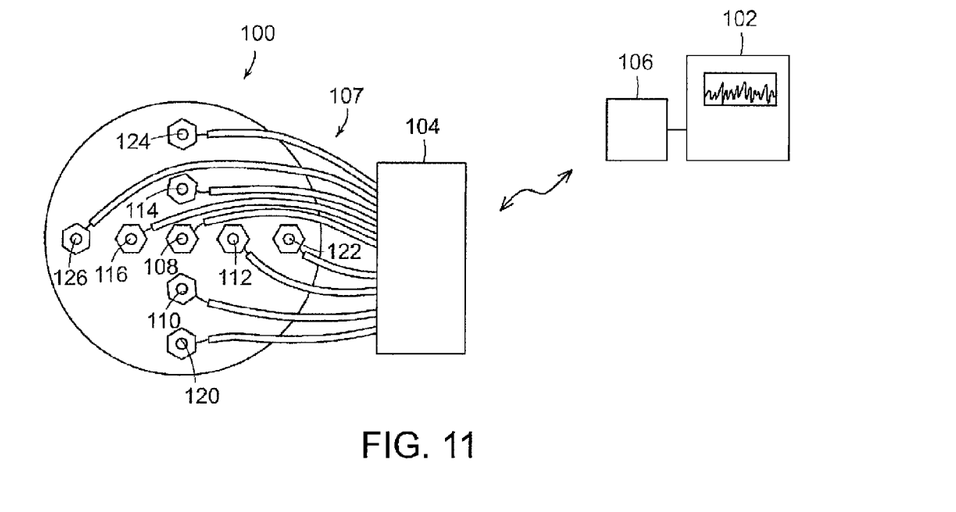
FIG. 11 shows an illustrative diagrammatic view of a biomedical sensor in accordance with a further embodiment of the invention wirelessly coupled to monitoring equipment.

FIG. 11 shows a biomedical sensor 100 in accordance with another embodiment of the invention that is attached to biomedical monitoring equipment 102 via a wireless communication system that includes a transceiver 104 attached to (or formed as part of) the biomedical sensor, and a transceiver 106 that is attached to the biomedical monitoring equipment 102. Similar to the embodiment of FIG. 10, the transmitter 104 includes multiple independent hard wire connections (as shown at 107) to each separate protruding electrode 108, 110, 112, 114, 116, 120, 122, 124, 126. Again, the signals from the electrodes may be analyzed in a variety of ways, including, for example, the five point method (using electrodes 108, 110, 112, 114 and 116), the nine point method (using electrodes 108, 110, 112, 114, 116, 120, 122, 124 and 16), and the quasi-bipolar method (wherein the electrodes 120, 122, 124 and 126 are electrically coupled together with electrode 108). Other arrangements of electrodes and analysis techniques may further be used, including for example, a thirteen point method that involves three concentric rings around a disc.

Figure 12:
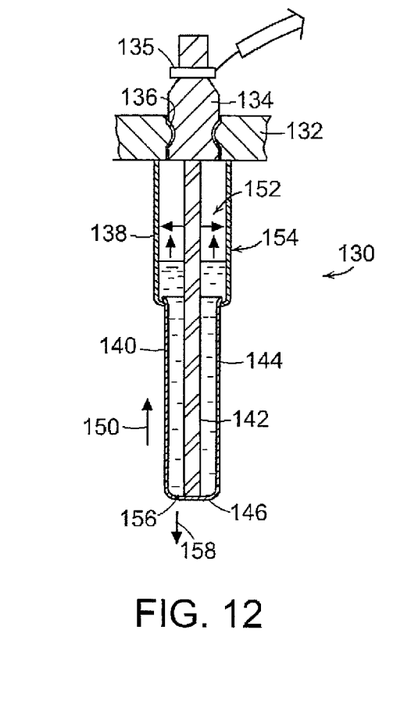
FIG. 12 shows an illustrative diagrammatic cross-sectional view of one protruding electrode in a biomedical sensor in accordance with a further embodiment of the invention.

FIG. 12 shows a protruding electrode 130 for a biomedical sensor in accordance with another embodiment of the invention, wherein the protruding electrode is coupled to a base 132 via a shaped post 134 that snap engages into an aperture 136 in the base 132. Wires may be coupled to the post 134 by any known technique such as by having a ring connector 135 attach to the top of the post 134 followed by soldering.

As also shown in FIG. 12, the protruding electrode 130 also includes a fixed protruding portion 138 and a resilient protruding portion 140. Within the protruding electrode is an elastomeric material 142 as well as fluid 144. When force is exerted on the distal end 146 of the electrode applying a force as shown at 150, then the elastomeric material 142 widens (as shown at 152), and in some embodiments, the fluid level of the fluid 144 rises (as shown at 154). The elastomeric material may preferably be an electrically conductive elastomeric material, and the fluid may preferably be an electrically conductive fluid such as a hydrogel. The use of such materials may further enhance electrical conductivity of the protruding electrode. In accordance with a further embodiment, as also shown in FIG. 12, each electrode may alternatively include a small aperture 156 in the distal end 146 of the electrode 130, out which a gel may flow (as shown at 158) when the electrode is compressed. Such a gel may facilitate electric conductivity between the sensor and the subject.

In accordance with further embodiments, there may be nano-scale or micro-scale end points on each of the protruding electrodes that may be used to make contact with the skin and affix the electrodes into place. The force by which the pins and sticky ends of the needle will be kept in place may be a micro-fluidic, gas, piezo, spring force or other mechanism that can propel the pins to retain contact if there is any movement involved. The distal tips of the protruding electrodes that contact the surface of a subject may be blunt, sharp or any combination, and may be shaped to improve surface contact. For example, the tip may be covered with a bed of small nails, micro-wires and/or carbon nano-tubes etc.

Figure 13:
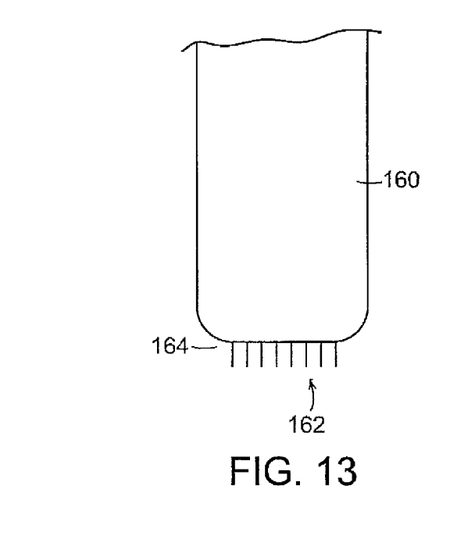
FIG. 13 shows an illustrative diagrammatic view of one protruding electrode in a biomedical sensor in accordance with a further embodiment of the invention.

As shown in FIG. 13 for example, in order to further enhance electrical contact with the skin of a subject, a protruding electrode 160 in a biomedical sensor in accordance with a further embodiment of the invention may include electrically conductive extensions 162 at the distal tip 164 of the electrode 160. The electrically conductive extensions 162 may be, for example, small short micro-wires or nano-tubes for engaging the skin of the subject while also enhancing electrical contact with the subject.

Electrodes of the invention may be used for the acquisition of biopotentials in clinical and research applications. The new electrodes may be used for recording the electroencephalogram (EEG), electrocardiogram (ECG), electromyogram (EMG), electrooculogram (EOG) etc. Use of the electrodes is also not limited to noninvasive recording; as they may also be used as implantable electrodes. They could also be used in any application where potentials need to be measured on a non-biological surface where movement artifact suppression is beneficial. Concentric electrodes take the differences of signals that are impressed on electrode elements very closely spaced (for EEG typically within 1.0 mm or less). The interference is nearly the same on both elements of the electrode and is automatically cancelled by common mode rejection. It may further be possible that electrodes of the invention are used in an application that permits or requires that a subject be mobile while monitoring their bio-potentials.

Those skilled in the art will appreciate that numerous modifications and variations may be made to the above disclosed embodiments without departing from the spirit and scope of the invention.

What is claimed is:

1. A biomedical sensor providing at least first, second and third electrical nodes for connection to medical equipment, said biomedical sensor comprising a plurality of protruding electrodes that extend from a common base, at least one of said protruding electrodes being coupled to the first electrical node, and at least two of said protruding electrodes being coupled to the second electrical node, at least one of said plurality of protruding electrodes being adjustable in length such that each of said plurality of protruding electrodes is adapted to contact a non-planar surface of a subject, said second and third electrical nodes being arranged in a functionally polar configuration to facilitate the determination of Laplacian voltage potentials $\Delta v_0$ at the first electrical node, wherein said third electrical node is provided by an outermost ring of conductors having a radius r that is employed to sense an outer region so as to provide a shielding function that prioritizes only signals below the biomedical sensor, wherein the shielding function is provided by using the approximation $$\Delta v_0 \cong \frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

2. The biomedical sensor as claimed in claim 1, wherein said at least one of said plurality of protruding electrodes that is adjustable in length is spring biased in an extended position.

3. The biomedical sensor as claimed in claim 1, wherein each of said plurality of protruding electrodes is spring biased in an extended position.

4. The biomedical sensor as claimed in claim 1, wherein said plurality of protruding electrodes are spaced from one another such that the protruding electrodes are adapted to contact a surface of a subject without interference by material that is attached to the contacting surface of the subject.

5. The biomedical sensor as claimed in claim 1, wherein said at least two of said protruding electrodes that are coupled to the second electrical node surround said at least one of said protruding electrodes that is coupled to the first electrical node.

6. A biomedical sensor providing at least first, second and third electrical nodes for connection to medical equipment, said biomedical sensor comprising a plurality of protruding electrodes that extend from a common base, at least one of said protruding electrodes being coupled to the first electrical node, and at least two of said protruding electrodes being coupled to the second electrical node, said plurality of protruding electrodes being spaced from one another such that the protruding electrodes are adapted to contact a surface of a subject without interference by material that is attached to the contacting surface of the subject, said second and third electrical nodes being arranged in a functionally polar configuration wherein said polar configuration includes an outer ring of connected protruding electrodes having a radius r that provides a shielding function to facilitate the determination of voltage potentials at the first electrical node, wherein said third electrical node is provided by the outer ring of connected protruding electrodes that are employed to sense an outer region such that a shielding function is provided that prioritizes only signals below the biomedical sensor, wherein the shielding function is provided by using the approximation $$\frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

7. The biomedical sensor as claimed in claim 6, wherein said plurality of protruding electrodes are adjustable in length such that each of said plurality of protruding electrodes may contact a non-planar surface.

8. The biomedical sensor as claimed in claim 6, wherein said at least two of said protruding electrodes that are coupled to the second electrical node surround said at least one of said protruding electrodes that is coupled to the first electrical node.

9. The biomedical sensor as claimed in claim 8, wherein said third electrical node includes at least four protruding electrodes.

10. The biomedical sensor as claimed in claim 9, wherein at least one of said protruding electrodes includes a hydrogel.

11. A biomedical sensor providing at least first, second and third electrical nodes for connection to medical equipment, said biomedical sensor comprising a plurality of protruding electrodes that extend from a common base, at least one of said protruding electrodes being coupled to the first electrical node, at least one of said protruding electrodes being coupled to the second electrical node, and at least one protruding electrode being coupled to the third electrical node, said plurality of protruding electrodes being spaced from one another such that the protruding electrodes are adapted to contact a surface of a subject without interference by material that is attached to the contacting surface of the subject, said first, second and third electrical nodes being arranged in a functionally tri-polar configuration to facilitate the determination of Laplacian voltage potentials $\Delta v_0$ at the first electrical node, wherein said third electrical node includes an outer ring of protruding conductors having a radius r that are employed to sense an outer region so as to provide a shielding function that prioritizes only signals below the biomedical sensor, wherein the shielding function is provided by using the approximation $$\Delta v_0 \cong \frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

12. The biomedical sensor as claimed in claim 11, wherein said plurality of protruding electrodes are adjustable in length such that each of said plurality of protruding electrodes may contact a non-planar surface.

13. The biomedical sensor as claimed in claim 11, wherein said plurality of protruding electrodes includes at least five protruding electrodes that are each coupled to an independent electrical node.

14. A biomedical sensor providing at least first, second and third electrical nodes for connection to medical equipment, said biomedical sensor comprising a plurality of protruding electrodes that extend from a common base, at least one of said protruding electrodes being coupled to the first electrical node, at least one of said protruding electrodes being coupled to the second electrical node, and at least one protruding electrode being coupled to the third electrical node, at least one of said plurality of protruding electrodes being adjustable in length such that each of said plurality of protruding electrodes is adapted to contact a non-planar surface of a subject, said first, second and third electrical nodes being arranged in a functionally tri-polar configuration wherein said tri-polar configuration includes an outer ring of connected protruding electrodes having a radius r that provides a shielding function to facilitate the determination of voltage potentials at the first electrical node, wherein said third electrical node is provided by the outer ring of connected protruding electrodes that are employed to sense an outer region such that the shielding function prioritizes only signals below the biomedical sensor, wherein the shielding function is provided by using the approximation $$\frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

15. The biomedical sensor as claimed in claim 14, wherein said at least one of said plurality of protruding electrodes that is adjustable in length is spring biased in an extended position.

16. The biomedical sensor as claimed in claim 14, wherein each of said plurality of protruding electrodes is spring biased in an extended position.

17. The biomedical sensor as claimed in claim 14, wherein each of said plurality of protruding electrodes includes an elastomeric spring that is biased in an extended position.

18. The biomedical sensor as claimed in claim 14, wherein each of said plurality of protruding electrodes includes an electrically conductive fluid within each of the protruding electrodes.

19. The biomedical sensor as claimed in claim 14, wherein each of said plurality of protruding electrodes includes a plurality of electrically conductive extensions that extend from a distal end of each said protruding electrode.

20. A method of applying a biomedical sensor to a patient, said biomedical sensor providing at least first, second and third electrical nodes for connection to medical equipment, and said biomedical sensor comprising a plurality of protruding electrodes that extend from a common base, said method comprising the steps of:
coupling at least one of the plurality of protruding electrodes to the first electrical node;
coupling at least some of the plurality of protruding electrodes to the second electrical node;
coupling at least some of the plurality of protruding electrodes to the third electrical node such that said first, second and third electrical nodes are arranged in a functionally polar configuration;
contacting a site of a subject with distal ends of each of said plurality of protruding electrodes, said step of contacting the site of the subject including passing distal ends of each of said plurality of protruding electrodes through material that is attached to a contacting surface at the site of the subject;
coupling the first, second and third electrical nodes to the medical equipment, said functionally polar configuration facilitating the determination of Laplacian voltage potentials $\Delta v_0$ at the first electrical node; and
sensing an outer region of the subject using the third electrical node that includes an outer ring of the plurality of protruding electrodes coupled to the third electrical node, the outer ring having a radius r, so as to provide a shielding function that prioritizes only signals below the biomedical sensor, wherein the shielding function is provided by using the approximation $$\Delta v_0 \cong \frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

21. The method as claimed in claim 20, wherein said material that is attached to the contacting surface at the site of the subject is hair.

22. The method as claimed in claim 20, wherein said step of contacting the site of the subject with the distal ends of each of said plurality of protruding electrodes further includes adjusting the length of at least one of said plurality of protruding electrodes such that each of said plurality of protruding electrodes may contact a non-planar surface at the site of the subject.

23. The method as claimed in claim 22, wherein said at least one of said plurality of protruding electrodes that is adjustable in length is spring biased in an extended position.

24. The method as claimed in claim 20, wherein said steps of coupling the first, second and third electrical nodes to the medical equipment includes sending wireless transmission signals.

25. A method of applying a biomedical sensor to a patient, said biomedical sensor providing at least first, second and third electrical nodes for connection to medical equipment, and said biomedical sensor comprising a plurality of protruding electrodes that extend from a common base, said method comprising the steps of:

coupling at least one of the plurality of protruding electrodes to the first electrical node;

coupling at least some of the plurality of protruding electrodes to the second electrical node;

coupling at some of the plurality of protruding electrodes to the third electrical node such that said first, second and third electrical nodes are arranged in a functionally polar configuration;

contacting a site of a subject with distal ends of each of said plurality of protruding electrodes, said step of contacting the site of the subject including adjusting the length of at least one of said plurality of protruding electrodes such that each of said plurality of protruding electrodes contacts a non-planar surface at the site of the subject;

coupling the first, second and third electrical nodes to the medical equipment, said third electrical node including an outer ring of protruding electrodes having a radius r that provides a shielding function to facilitate the determination of voltage potentials at the first electrical node such that a shielding function prioritizes only signals below the biomedical sensor, wherein the shielding function is provided by using the approximation $$\frac{1}{3r^2}\{16(v_{Second\,node} - v_{First\,node}) - (v_{Third\,node} - v_{First\,node})\}$$

where $v_{First\,node}$ represents the voltage potential at the first electrical node, $v_{Second\,node}$ represents the voltage potential at the second electrical node, and $v_{Third\,node}$ represents the voltage potential at the third electrical node.

26. The method as claimed in claim 25, wherein said at least one of said plurality of protruding electrodes that is adjustable in length is spring biased in an extended position.

27. The method as claimed in claim 25, wherein said step of contacting the site of the subject with the distal ends of each of said plurality of protruding electrodes further includes receiving between the distal ends of each of said plurality of protruding electrodes, material that is attached to a contacting surface at the site of the subject.

28. The method as claimed in claim 27, wherein said material that is attached to the contacting surface at the site of the subject is hair.

29. The method as claimed in claim 25, wherein said steps of coupling the first and second electrical nodes to the medical equipment includes sending wireless transmission signals.

* * * * *